US00PP25419P2

(12) United States Plant Patent
Hartman

(10) Patent No.: US PP25,419 P2
(45) Date of Patent: Apr. 7, 2015

(54) ***CALADIUM* PLANT NAMED 'SCARLET FLAME'**

(50) Latin Name: *Caladium×hortulanum*
Varietal Denomination: Scarlet Flame

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 115 days.

(21) Appl. No.: 13/986,545

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Scarlet Flame', characterized by its compact, upright and uniformly mounding plant habit; vigorous growth habit and rapid growth rate; lance-type leaves that are dark green in color with rose red-colored venation and interveinal areas and pink-colored blotches; and good landscape performance.

4 Drawing Sheets

Botanical designation: *Caladium×hortulanum.*
Cultivar denomination: 'SCARLET FLAME'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Scarlet Flame'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in June, 2006 in Avon Park, Fla. of *Caladium×hortulanum* 'John Peed', not patented, as the female, or seed, parent with *Caladium×hortulanum* 'Candyland', disclosed in U.S. Plant Pat. No. 18,766, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2007.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since Apr. 15, 2008 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Scarlet Flame'. These characteristics in combination distinguish 'Scarlet Flame' as a new and distinct *Caladium* plant:

1. Compact, upright and uniformly mounding plant habit.
2. Vigorous growth habit and rapid growth rate.
3. Lance-type leaves that are dark green in color with rose red-colored venation and pink and rose red-colored spots and blotches.
4. Good landscape performance.

Plants of the new *Caladium* differ primarily from plants of the female parent, 'John Peed', in leaf shape and color as plants of 'John Peed' have fancy-type leaves that are dark green in color with red-colored venation. In addition, plants of the new *Caladium* are more compact than plants of 'John Peed'.

Plants of the new *Caladium* differ primarily from plants of the male parent, 'Candyland', in the following characteristics:

1. Plants of the new *Caladium* are more compact than plants of 'Candyland'.
2. Plants of the new *Caladium* and 'Candyland' differ in leaf coloration as leaves of plants of 'Candyland' were white to grey-green in color with random pink-colored spots and green-colored margins.
3. Plants of the *Caladium* and 'Candyland' differ in leaf petiole coloration as leaf petioles of plants of 'Candyland' are tan in color with dark green-colored stippling, streaks and tessellations.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* were denser than and not as open as plants of 'Florida Sweetheart'.
2. Plants of the new *Caladium* and 'Florida Sweetheart' differed in leaf coloration as leaves of plants of 'Florida Sweetheart' had lighter rose red-colored centers and dark green-colored margins.

Plants of the new *Caladium* can be compared to plants of *Caladium×hortulanum* 'Lance Whorton', not patented. In side-by-side comparisons, plants of the new *Caladium* differed primarily from plants of 'Lance Whorton' in the following characteristics:

1. Plants of the new *Caladium* grew faster and produced finished plants about one week earlier than plants of 'Lance Whorton'.
2. Plants of the new *Caladium* were denser than and not as open as plants of 'Lance Whorton'.
3. Plants of the new *Caladium* had broader leaves than plants of 'Lance Whorton'.
4. Plants of the new *Caladium* and 'Lance Whorton' differed in leaf coloration as leaves of plants of 'Lance Whorton' were dark green in color with pink-colored spots, lighter green-colored blotches and rose red-colored venation.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Scarlet Flame' in a 15-cm container and grown in a shadehouse.

The photograph at the top of the second sheet is a comparison view of typical plants of 'Scarlet Flame' grown in 15-cm containers; the plant on the left has not had its tuber de-eyed and the plant on the right has had its tuber de-eyed prior to planting.

The photograph at the bottom of the second sheet is a close-up view of typical inflorescences of 'Scarlet Flame'.

The photograph at the top of the third sheet is a close-up view of a typical freshly-harvested tuber and roots of 'Scarlet Flame'.

The photograph at the top of the third sheet is a view of typical plants of 'Scarlet Flame' grown in an open field.

The photograph at the top of the fourth sheet is a comparison view of typical potted plants of 'Florida Sweetheart' (left), 'Scarlet Flame' (center) and 'Lance Whorton' (right).

The photograph at the bottom of the fourth sheet is a comparison view of typical potted plants of the male parent, 'Candyland' (left), 'Scarlet Flame' (center) and the female parent, 'John Peed' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were nine weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Scarlet Flame'.

Parentage:

*Female, or seed, parent.*—*Caladium×hortulanum* 'John Peed', not patented.

*Male, or pollen, parent.*—*Caladium×hortulanum* 'Candyland', disclosed in U.S. Plant Pat. No. 18,766.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to round in shape. Height: About 3.5 cm. Diameter: About 4.4 cm. Segment height: About 2.8 cm. Segment diameter: About 2.2 cm. Texture: Thick, starchy; somewhat brittle. Color: Epidermis, freshly-harvested: Close to 199A and 200A. Epidermis, dried: Close to 200A. Cortical tissue: Close to 155C to 155D and 4D. Axillary buds: Close to 37C. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounding plant habit; vigorous and dense growth habit; rapid growth rate, potted plants in finished or saleable form in about seven to eight weeks after planting tubers; leaf petioles and leaves arise from one or more growing points on tubers; petioles mostly upright and arching outwardly with development.

*Plant height, from soil level to top of foliar plane, shadehouse-grown potted plants.*—About 21 cm to 26 cm.

*Plant height, from soil level to top of inflorescences, shadehouse-grown potted plants.*—About 30.2 cm.

*Plant diameter or spread, shadehouse-grown potted plants.*—About 44 cm to 50 cm.

*Number of clumps per plant, shadehouse-grown potted plants.*—About three to four from de-eyed tubers.

*Cataphylls, shadehouse-grown potted plants.*—Length: About 4.9 cm to 6.5 cm. Width: About 1 cm to 2 cm. Shape: Wedge-shaped. Apex: Acuminate. Base: Sheathing the stem. Color, outer surface: Close to 170D tinged with close to 147C and variably to densely streaked with close to 200A tinged with close to 147A; with development, color becoming closer to 200A to 200B. Color, inner surface: Close to N155C; outer surface colors and patterns visible.

Foliage description:

*Arrangement and type.*—Alternate; simple; lance-type.

*Length, shadehouse-grown potted plants*.—About 15 cm to 17.5 cm.

*Width, shadehouse-grown potted plants, flattened*.—About 11.5 cm to 13.2 cm.

*Shape*.—Broadly ovate to somewhat deltoid.

*Apex*.—Acuminate.

*Base*.—Sagittate, peltate; cordate.

*Margin*.—Entire; wavy with broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing and fully expanded leaves, upper surface: Background color: Close to 147A to darker than 147A; interveinal areas with random spots and blotches, close to 55C to 55D, 63C, 69A, 185C to 185D, and 187B. Basal notch: Close to 187A. Venation: Close to 53A to 53B and 185B. Developing and fully expanded leaves, lower surface: Background color: Close to 147B and 191A; interveinal areas with random spots and blotches, close to 63C to 63D, 184C to 184D and 185D; margins, close to 187A. Basal notch: Close to 187A. Midvein: Close to 182D streaked with close to 184B to 184C. Primary venation: Close to 147C surrounded by close to 184C.

*Petiole*.—Aspect: Initially upright and straight; with development, leaning outwardly and curving; flexible. Length, shadehouse-grown potted plants: About 18.5 cm to 21 cm. Diameter, distal, shadehouse-grown potted plants: About 3.5 mm to 4 mm. Diameter, proximal, shadehouse-grown potted plants: About 8.5 mm to 10 mm. Color, shadehouse-grown potted plants: Close to N170D and 185D densely stippled, streaked and tessellated with close to 200A tinged with close to 147A; distally, close to 185D and 186C. Wing length, shadehouse-grown potted plants: About 3 cm to 4.5 cm. Wing diameter, shadehouse-grown potted plants: About 6 mm to 9 mm. Wing color, shadehouse-grown potted plants, outer surface: Close to N170D and 195D densely stippled and streaked with close to 200A tinged with close to 147A. Wing color, shadehouse-grown potted plants, inner surface: Close to N155C; outer surface colors and patterns visible.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like fragrance with camphor-like notes.

*Natural flowering season and flower longevity*.—Plants of the new *Caladium* typically flower during the spring or early summer in central Florida; flowers develop about eight weeks after growth commences; inflorescences last about three days before fading; inflorescences persistent.

*Spathe*.—Length, overall: About 10.5 cm. Length, distal open portion: About 7.7 cm. Length, proximal closed portion: About 3.2 cm. Width, distal open portion: About 3.9 cm. Width, at constriction: About 1.5 cm. Width, proximal closed portion: About 2.3 cm. Shape: Ovate. Apex: Acute. Base: Tapering to the peduncle. Margin: Entire. Texture, front and rear surfaces: Smooth, glabrous. Color, front surface: Distal open portion: Close to 157D variably streaked with close to 59C to 59D; towards the apex, tinged with close to 36D; center, tinged with close to 193A to 193B; with development, color becoming closer to 199C. Proximal closed portion: Close to 138B and 147C; towards the base, deeply tinged with close to N186A; color does not change with development. Color, rear surface: Distal open portion: Close to 160D tinged with close to 150C to 150D; apex, tinged with close to 36D; center, close to 144A tinged with close to 160D; overall occasionally streaked with close to 59B to 59C. Proximal closed portion: Close to 183C to 183D and 184B to 184C with areas of close to 147B to 147C and 146A to 146B.

*Spadix*.—Length: About 7.8 cm. Length, male flower zone: About 4.8 cm. Length, sterile zone: About 8 mm. Length, female flower zone: About 2.2 cm. Diameter, male flower zone: About 1 cm. Diameter, sterile flower zone: About 6.5 mm. Diameter, female flower zone: About 1 cm. Shape: Columnar, spindle-shaped. Apex: Obtuse. Base: Obtuse. Aspect: Upright. Color, mature, male zone: Close to 159D. Color, mature, sterile zone: Close to 155D. Color, mature, female zone: Close to 155B and 4A. Male flowers: Quantity per spadix: About 225. Shape: Obovate. Height: About 3 mm. Diameter: About 3.5 mm. Pollen amount: Abundant. Pollen color: Close to 4C. Female flowers: Quantity per spadix: About 220. Shape: Obovate. Height: About 2.5 mm. Diameter: About 1 mm. Stigma color: Close to 155B and 4A. Ovary color: Close to 155B.

*Scape*.—Length: About 19.7 cm. Diameter: About 6 mm. Strength: Sturdy; flexible. Aspect: Mostly erect. Texture: Smooth, glabrous; glaucous. Color: Close to 147A to 147B, overall streaked, mottled and tessellated with close to 200A, 182B and 147A; distally, tinged and streaked with close to 183C and 200A.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Scarlet Flame' as illustrated and described.

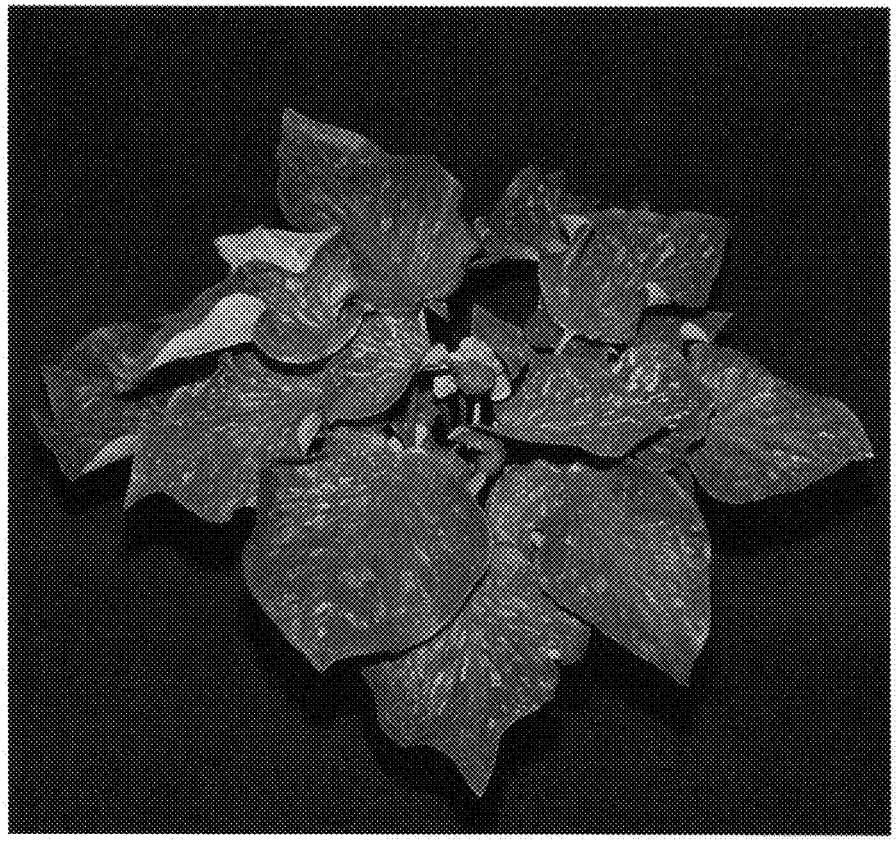

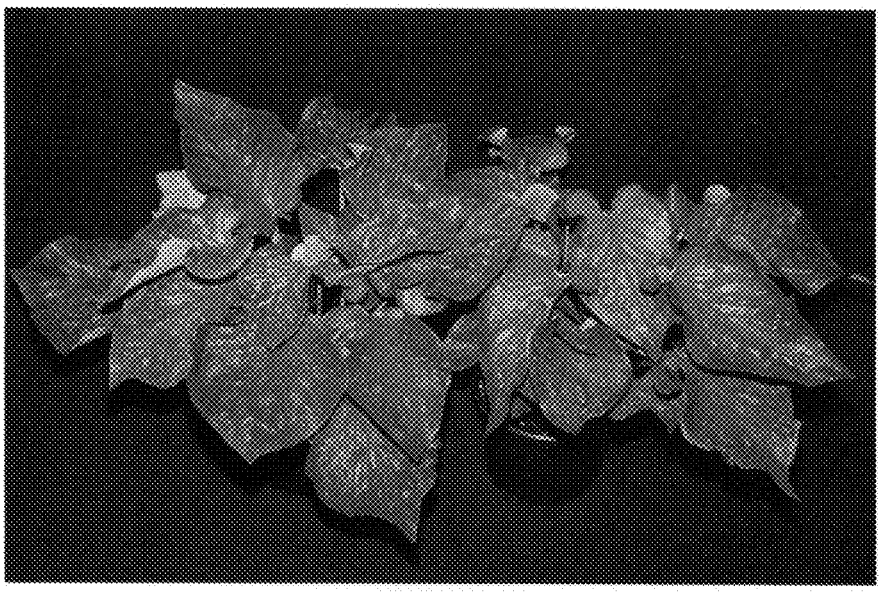
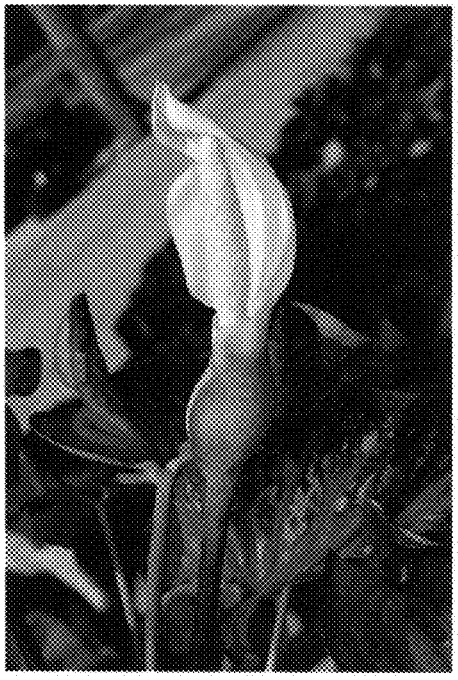

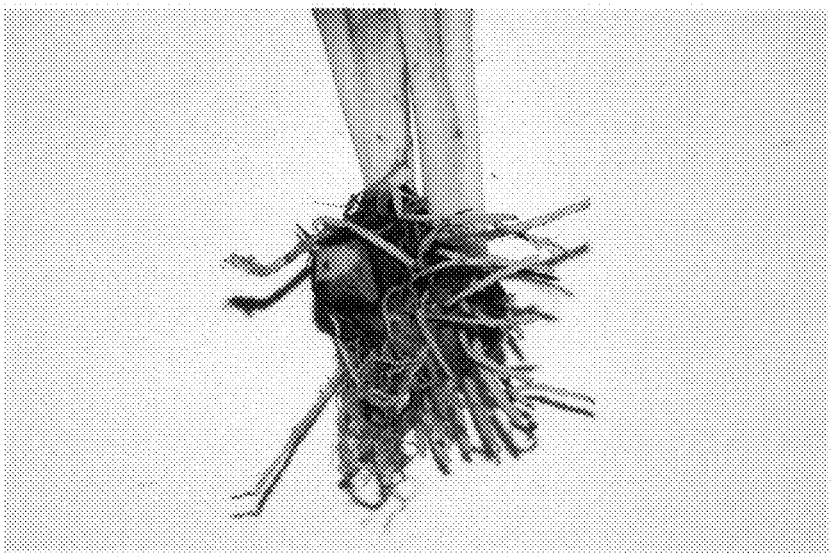
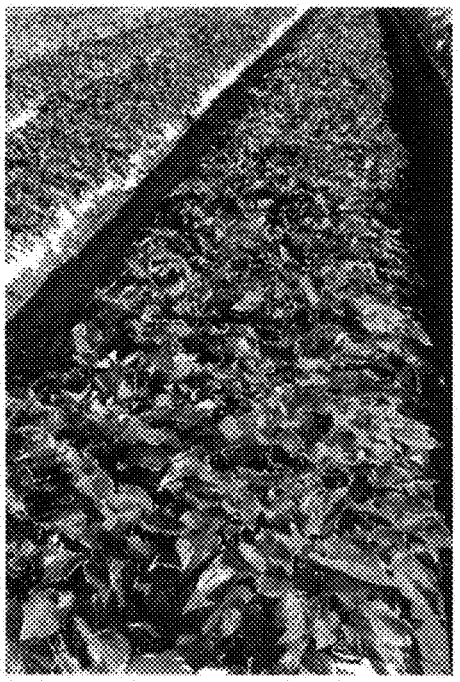

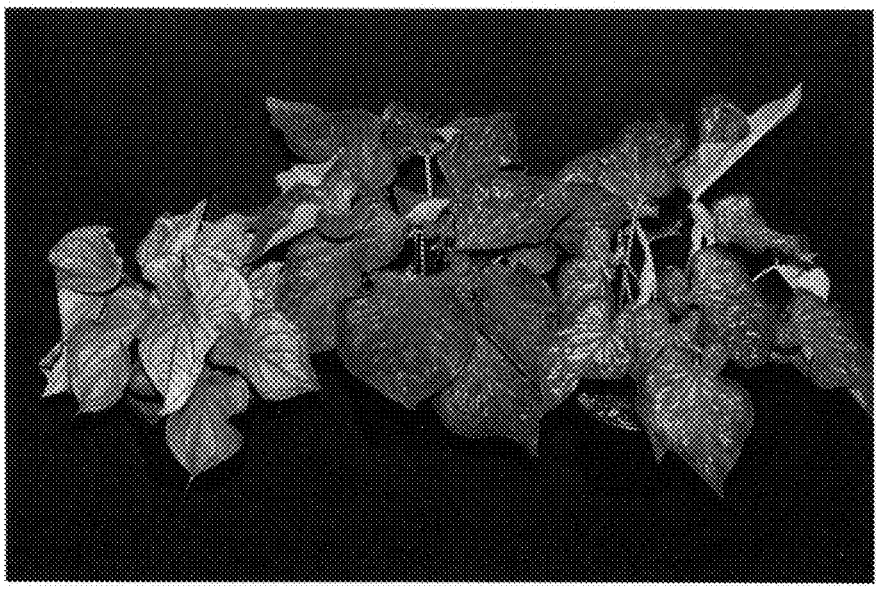
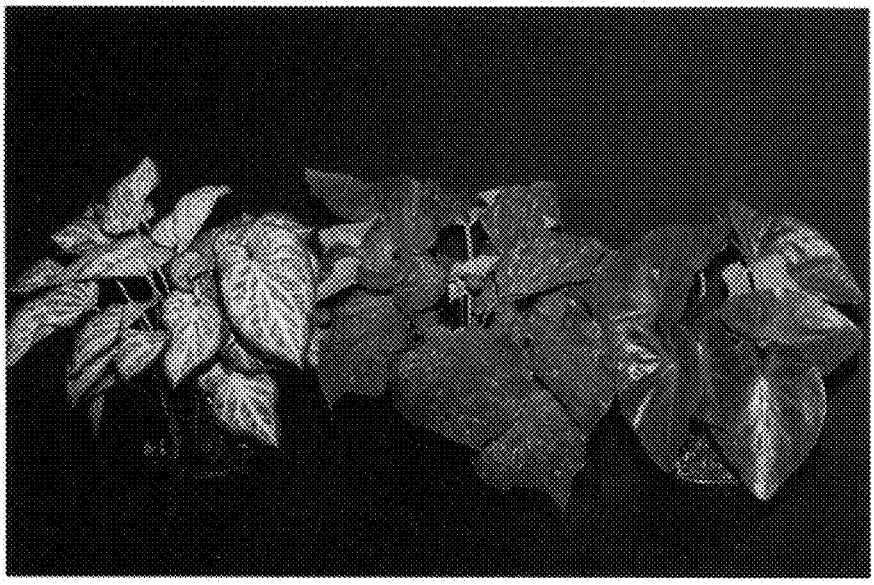

* * * * *